United States Patent [19]
Wang

[11] Patent Number: 6,011,066
[45] Date of Patent: Jan. 4, 2000

[54] METHOD FOR TREATING SEPTIC SHOCK

[75] Inventor: Soo-Ray Wang, Talpei, Taiwan

[73] Assignee: Veterans General Hospital-Taipei, Taipei, Taiwan

[21] Appl. No.: 09/017,433

[22] Filed: Feb. 2, 1998

[51] Int. Cl.⁷ .................... A61K 31/52; A61K 31/195
[52] U.S. Cl. .................... 514/561; 518/563; 518/564; 518/566; 518/567; 518/616; 518/626; 518/629; 518/649; 518/653; 518/654; 518/663; 518/673; 514/674
[58] Field of Search .................... 514/561, 563, 514/564, 566, 567, 616, 626, 629, 649, 653, 654, 663, 673, 674

[56] References Cited

U.S. PATENT DOCUMENTS

| | | | |
|---|---|---|---|
| 4,388,318 | 6/1983 | Koyama et al. | 424/251 |
| 4,822,776 | 4/1989 | Cerami et al. | 514/21 |
| 5,028,627 | 7/1991 | Kilbourn et al. | 514/565 |
| 5,068,314 | 11/1991 | Nakamura et al. | 530/317 |
| 5,162,571 | 11/1992 | Shiraishi et al. | 514/237.5 |
| 5,171,739 | 12/1992 | Scott | 514/12 |
| 5,175,183 | 12/1992 | Brooks et al. | 514/438 |
| 5,286,739 | 2/1994 | Kilbourn et al. | 514/400 |
| 5,306,710 | 4/1994 | Wei | 514/12 |
| 5,334,380 | 8/1994 | Kilbourn et al. | 424/85.2 |
| 5,374,651 | 12/1994 | Kibourn et al. | 514/400 |
| 5,436,270 | 7/1995 | Wang | 514/565 |
| 5,502,055 | 3/1996 | Wang | 514/250 |
| 5,530,113 | 6/1996 | Christ et al. | 536/123.13 |
| 5,534,545 | 7/1996 | Kilbourn et al. | 514/565 |
| 5,576,350 | 11/1996 | Wang | 514/565 |
| 5,594,113 | 1/1997 | Wainwright et al. | 530/395 |
| 5,656,608 | 8/1997 | Schneider et al. | 514/42 |

FOREIGN PATENT DOCUMENTS

WO9411370  5/1994  WIPO .

OTHER PUBLICATIONS

Souba, W.W., et al., "The role of glutamine in maintaining a healthy gut and supporting the metabolic response to injury and infection", J. Surg. Res. 1990 Apr.; 48(4):383–391.

Ardawi, M.S., "Effect of glutamine–enriched total parenteral nutrition on septic rats", Clin. Sci. (Colch) 81 (2): 215–222 (Aug. 1991).

Clowes, et al. "Effects of parenteral alimentation on amino acid metabolism in septic patients", Surgery, vol. 88, No. 4, pp. 531–543, Oct. 1980.

*Primary Examiner*—Frederick Krass
*Attorney, Agent, or Firm*—Christie, Parker & Hale, LLP

[57] ABSTRACT

A method for the treating septic shock in a patient comprises administering to the patient a therapeutically-effective amount of a composition comprising a compound having the formula (I):

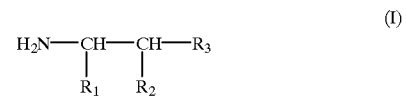

wherein $R_1$ is hydrogen, hydroxyl, carboxyl, amino or $C_1$–$C_8$ alkyl; $R_2$ is hydrogen, hydroxyl, amino or $C_1$–$C_8$ alkyl; and $R_3$ is hydrogen, hydroxyl, carboxyl, amino, $C_1$–$C_8$ alkyl, substituted or unsubstituted phenyl, amide, $C_3$–$C_8$ aminoalkyl, or $C_1$–$C_8$ aminoalkylcarbonyl; or a therapeutically-effective salt, ester or solvate thereof. Particularly preferred compounds for use in the present invention include butylamine, propylamine, diaminopropane, diaminobutanone, tyrosine, threonine, asparagine, and aspartate.

29 Claims, No Drawings

METHOD FOR TREATING SEPTIC SHOCK

FIELD OF THE INVENTION

The present invention relates to a method for treating shock. More particularly, it relates to a method involving administering a therapeutically-effective amount of a composition to a patient to treat septic shock.

BACKGROUND OF THE PRESENT INVENTION

Septic shock is a life-threatening complication of bacterial infection. The reported number of incidences has steadily increased since the 1930's, and septic shock is presently the most common cause of mortality and morbidity in non-coronary intensive care units in the U.S. The yearly mortality due to septic shock in the U.S. is as high as 200,000.

Bacteremia is typically defined as bacteria in the bloodstream and is usually determined by a positive blood culture. Sepsis refers to the physiological alterations and clinical consequences of the presence of microorganisms or their products in the bloodstream or tissues. When sepsis is associated with hypotension and signs of poor tissue perfusion, it is called septic shock. Septic shock has traditionally been recognized as a consequence of infection with gram-negative bacteria, but it may also be caused by gram positive bacteria, fungi, viruses, and protozoa.

The pathogenesis of septic shock is complex and not fully understood. One of the complicating factors is that overlapping, and sometimes even opposing, effects can be present. Various gram-negative microorganisms can generate endotoxins which can release potential mediators such as IL-1 and TNF-$\alpha$ that would act on vasculature and myocardium. Studies in both animals and humans have shown that endotoxin is the primary factor that precipitates the shock state. Endotoxin is a lipopolysaccharide molecule that is contained in the cell wall of all gram-negative bacteria. It is released from a focus of infection when gram-negative bacteria are phagocytized by either circulating macrophages or cells of the reticuloendothelial system.

In the past, the conventional approach in treating septic shock has been to administer intravenous injection of excess amounts of glucocorticolds, such as methylprednisolone, at dosage of about 30 mg per kilogram of body weight. However, this method has been proven ineffective in two double-blind control studies.

It has long been known that endotoxins activate the complement cascade, and, via the release of components of the complement system, many of the effects of sepsis occur. After invading the bloodstream, microorganisms begin a cascade of events leading to the release of microbial toxins and harmful host mediators that produce sepsis. The early mediators are thought to consist of microorganism-oriented exotoxins and endotoxins, and host effectors such as neutrophils and macrophages, which produce cytokines such as tumor necrosis factor (TNF) and interleukin-1 (IL-1). The release of cytokines in small amounts is normally a protective response. In the presence of endotoxins, however, the massive release of TNF and subsequent activation of immune cells can lead to persistent uncontrolled systemic inflammation, resulting in wide tissue injury and metabolic derangement.

Once released, cytokines trigger a complex array of further host substances, such as prostaglandins, coagulative and fibrinolytic cascades, nitric oxide (NO), endorphins, interferons, and platelet-activating factors. Overall, this network of mediators and toxins affect the systemic and pulmonary vasculatures, the myocardium, and the structures of endothelium, producing hypotension and resulting in death. NO is a potent endothelium-derived relaxing factor (EDRF); it may play a major role in the regulation of microcirculation. In the past, in vitro and in vivo studies have suggested that endotoxin-induced loss of vascular responsiveness is due to activation of NO which is synthesized from L-arginine and can be blocked by NO synthase inhibitors, L-arginine analogues, such as N-nitro-L-arginine methyl ester (L-NAME). Several studies have shown that NO has a major effect on cardiovascular performance in endotoxemia. Inhibition of NO synthesis has thus been considered as being a potentially useful method in the treatment of sepsis.

None of the prior art methods have a proven record of success. Therefore, other therapies must be considered to improve survival rate and reduce morbidity. In recent years, immunotherapy and immunoprophylaxis have been advocated, and it has been suggested that human antiserum and monoclonal antibodies can be effective against endotoxins and TNF reduced death from gram-negative bacterial infection.

Several U.S. patents have discussed the prophylaxis and treatment of endotoxin-induced shock. U.S. Pat. No. 4,388, 318 ('318 patent) issued to Kayama, et al, discloses a method of treating endotoxin shock with a pyrimido-pyrimidine derivative. The basis of the '318 patent is that central adrenergic neurons influence peripheral sympathetic nerve activity and thus cardiovascular regulation. The inhibition of alpha adrenergic receptors in vasomotor centers mediates a decrease in blood pressure, heart rate and peripheral sympathetic activity. Since $E.$ $coli$ endotoxin may exert its hypotensive effect by activating the central autonomic blood pressure regulatory circuits, the administering of a pyrimido-pyrimidine derivative, which has a central hypertensive effect acting on the medullary cardiovascular regulatory systems, may stimulate central alpha adrenergic receptors leading to inhibition of brain stem sympathetic pathways that participate in the baroreceptor reflex system.

U.S. Pat. No. 4,822, 776 ('776 patent), issued to Ceraml and Kawakami, discloses an endotoxin-induced mediator substance, which purportedly may be utilized as a screening agent to test for potentially effective anti-shock agents. In the '776 patent, it was suggested that the mediator substance can be used to produce antibodies to themselves in rabbits, goats, sheep, chickens, or other mammals. These antibodies may be used as test agents for the presence of the mediator substance, and can be administered in pharmaceutical compositions in response to shock produced by viruses, bacteria, protozoa, etc.

U.S. Pat. No. 5,028, 627 ('627 patent) discloses a method of using arginine derivatives as arginine antagonists for prophylaxis or treatment of systemic hypertension associated with nitric oxide production or endothelial derived relaxing factor. One embodiment of the inhibitor disclosed in the '627 patent is $N^G$-substituted arginine or an $N^G,N^G$-disubstituted arginine, which is administered to an animal that is potentially developing or having a systemic hypotension induced by a biological response modifier. The '627 patent follows the commonly accepted belief that arginine is the physiological precursor of nitric oxide synthesis, and concludes that substituted or disubstituted arginine antagonists, such as $N^G$-aminoarginine, $N^G$-nitroarginine, $N^G$-methylarginine, $N^G$-ethylarginine, $N^G$-propylarginine, $N^G$-butylarginine, etc., could inhibit the production of nitrogen oxide from arginine in an animal or patient, thus obviating the hypotensive effects of nitrogen oxide.

U.S. Pat. No. 5,068,314 discloses an arginine derivative, which functions as a lipopolysaccharide-binding polypeptide, for removing endotoxin. U.S. Pat. No. 5,175, 183 discloses the use of lipoxygenase-inhibiting compounds in treating disease states, including endotoxin shock. The compounds disclosed include N-aryl, N-heteroaryl, N-arylalkyl, N-heteroarylalkyl, N-arylcyclopropyl, and N-heteroaryl-cyclopropyl-N'-hydroxyurea compounds. U.S. Pat. No. 5,171,739 discloses a method for treating and preventing endotoxin-associated shock using a BPI protein that is effective in binding endotoxins. U.S. Pat. No. 5,162, 571 discloses phenol derivatives that have therapeutic and prophylactic activities against endotoxin shock.

As indicated above, traditional approaches to the treatment of septic shock have mainly involved administering glucocorticoids, LPS-antibodies, NO-synthase inhibitors, and arginine derivatives (as arginine antagonists). However, none of these methods has been proven clinically effective. One of the most difficult problems in developing an effective treatment method lies in the fact that the mechanisms causing the endotoxin-induced shocks have not been fully understood, or may have been incorrectly stated.

It has previously been discovered that several compounds can effectively prevent the occurrence of endotoxin-induced shock. U.S. Pat. No. 5,436,270 ('270 patent) discloses arginine, which, when intraperitorially injected 24 hours prior to lipopolysaccharide injection, can significantly prevent lipopolysacchande-induced mortality. U.S. Pat. No. 5,502,055 and U.S. Pat. No. 5,576,350 disclose putrescine and spermidine, respectively, which when administered in a manner similar to that used for arginine, can also significantly prevent lipopolysaccharide-induced mortality.

SUMMARY OF THE PRESENT INVENTION

The present invention is directed to an improved method for the treatment of septic shock. The method involves administering to a patient a therapeutically-effective amount of a composition comprising at least one compound having the formula (I):

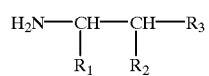

(I)

wherein:
$R_1$ is hydrogen, hydroxyl, carboxyl, amino, or $C_1$–$C_8$ alkyl;
$R_2$ is hydrogen, hydroxyl, amino, or $C_1$–$C_8$ alkyl; and
$R_3$ is hydrogen, hydroxyl, carboxyl, amino, $C_1$–$C_8$ alkyl, phenyl, substituted phenyl, amide, $C_3$–$C_8$ aminoalkyl, or $C_1$–$C_8$ aminoalkylcarbonyl;
or a therapeutically-effective salt, ester or solvate thereof.

DETAILED DESCRIPTION OF THE INVENTION

The present invention is directed to a method for treating septic shock in a patient. In one embodiment, the method comprises administering to the patient a therapeutically-effective amount of a composition comprising at least one compound having the formula (I):

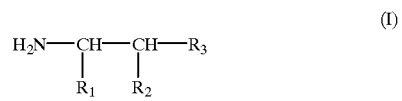

(I)

wherein:
$R_1$ is hydrogen, hydroxyl, carboxyl, amino, or $C_1$–$C_8$ alkyl;
$R_2$ is hydrogen, hydroxyl, amino, or $C_1$–$C_8$ alkyl; and
$R_3$ is hydrogen, hydroxyl, carboxyl, amino, $C_1$–$C_8$ alkyl, phenyl, substituted phenyl, amide, $C_3$–$C_8$ aminoalkyl, or $C_1$–$C_8$ aminoalkylcarbonyl;
or a therapeutically-effective salt, ester or solvate thereof.

Preferred compounds of the invention include those of formula (I) wherein $R_3$ is hydrogen, hydroxyl, carboxyl, amino, $C_1$–$C_8$ alkyl, phenyl, substituted phenyl, amide, or $C_1$–$C_8$ aminoalkylcarbonyl, and salts, esters and solvates thereof. Other preferred compounds include those of formula (I) wherein $R_1$ is hydrogen, hydroxyl, amino, or $C_1$–$C_8$ alkyl, and $R_3$ is hydrogen, hydroxyl, carboxyl, amino, $C_1$–$C_8$ alkyl, phenyl, substituted phenyl, or amide, and salts, esters and solvates thereof. Still other preferred compounds include those of formula (I) wherein $R_1$ is hydrogen, particularly those wherein $R_1$ is hydrogen and $R_2$ is hydrogen, and salts, esters, and solvates thereof.

Particularly preferred compounds according to the invention include butylamine, propylamine, diaminopropane, diaminobutanone, tyrosine, threonine, asparagine, and aspartate, and therapeutically effective salts, esters, solvates and substitution products thereof Propylamine and n-butylamine are particularly preferred.

As used herein, the term "amino" includes primary, secondary, and tertiary amines.

As used herein, the term "substituted phenyl" refers to a phenyl group substituted by one or more substituents selected from hydroxyl, halogen, $C_1$–$C_4$ alkyl, and amino. A preferred substituted phenyl group is hydroxy-phenyl, more preferably p-hydroxy-phenyl.

As used herein, the term "amide" refers to the group— $C(O)NR_5R_6$, wherein $R_5$ and $R_6$ are, independently, hydrogen or $C_1$–$C_4$ alkyl.

As used herein, the term "aminoalkyl" refers to the group—$(CH_2)_n$—$NR_7R_8$, wherein n is a positive integer ranging from 1 to about 8, more preferably 3 to 8, still more preferably 4 to 8, and $R_7$ and $R_8$ are, independently, hydrogen or $C_1$–$C_4$ alkyl.

As used herein, the term "aminoalkylcarbonyl" refers to the group—$C(O)$—$(CH_2)_n$—$NR_9R_{10}$, wherein n is a positive integer ranging from 1 to about 8, more preferably 1 to 4, and $R_9$ and $R_{10}$ are, independently, hydrogen or $C_1$–$C_4$ alkyl.

As used herein, the term "aspartate" refers to salts or esters of asparताric acid.

As used herein, the term "substitution product" refers to structurally-related compounds in which one or more hydrogen atoms are replaced with one or more suitable substituents. For example, the term "substitution product of propylamine" refers to all compounds that are structurally related to propylamine having one or more hydrogen atoms replaced with suitable substituents. The term "suitable substituent" refers to any substituent. e.g., atom or other functional group, which, when included on a compound, allows the compound to retain the functional properties with respect to the treatment of septic shock that the compound has when not substituted. Suitable substituents include, but are not limited to, halogens (e.g., chlorine, fluorine, bromine and iodine), hydroxyl groups, and $C_1$–$C_4$ alkyl groups.

A therapeutically-effective amount of the composition is an amount sufficient to reduce, inhibit or prevent shock induced by endotoxins or bacteremia in a patient. For example, for propylamine, a therapeutically-effective amount is preferably at least about 0.05 ml/kg of body weight, more preferably at least about 1.5 ml/kg of body weight, still more preferably from about 1.5 to 15 ml/kg, and still more preferably from about 5 to 15 ml/kg. For n-butylamine, a therapeutically-effective amount is preferably at least about 0.05 ml/kg of body weight, more preferably at least about 1.5 ml/kg of body weight, still more preferably from about 1.5 to 15 ml/kg, and still more preferably from about 5 to 15 ml/kg. As used herein, the term "patient" refers to any animal, in particular, mamals, for example, humans.

Preferably, the composition further comprises a pharmaceutically acceptable carrier; a nonlimiting example is phosphate-buffered saline.

According to the present method, the composition can be administered parenterally, for example, in sterile liquid dosages forms, such as by intraperitoneal injection. Alternatively, the composition can be administered orally, for example in liquid dosage forms, such as elixirs, syrups and suspensions, or in solid dosage forms, such as capsules, tablets and powders. When administered orally, the composition preferably comprises a pharmacutically acceptable carrier, for example, a filler.

The present invention will now be described more specifically with reference to the following examples. It is to be noted that the following examples, which include preferred embodiments of this invention, are presented herein for purposes of illustration and description; they are not intended to be exhaustive or to limit the invention to the precise form disclosed.

EXAMPLE 1

The mice used in this study were male balb/c having a body weight around 20 g. Each mouse was intraperitoneally injected with *E. coli* lipopolysaccharide (LPS) 0.7 mg in 1 ml PBS buffer (pH 7.4) containing one of the following compounds: L-arginine 90 mg (0.5 mMole), ornithine 70 mg (0.5 mMole), putrescine 10 mg, spermine 30 mg, spermidine 10 mg, L-lysine 30 mg, n-butylamine 1 ml of 0.1%, L-alanine 100 mg, diaminopropane 10 mg, diaminobutanone 30 mg, and propylamine 0.3%. The dose of each compound was predetermined to be the highest safe dose (with the exception of n-butylamine, which was 0.3%, see Table 3) causing no mortality in at least 10 mice. The *E. coli* LPS was serotype 0111:B4 obtained from Sigma (St. Louis, Mo.). The survival rates were observed for three days and are shown in Table 1. The tests revealed that n-butylamine provides the best protection, with propylamine providing the second-best protection.

TABLE 1

|  | No. of Mice Tested | No. of Mice Survived | % | Ranking |
|---|---|---|---|---|
| n-Butylamine | 10 | 10 | 100 | 1 |
| Propylamine | 10 | 7 | 70 | 2 |
| Putrescine | 10 | 5 | 50 | 3 |
| Diaminobutanone | 10 | 3 | 30 | 4 |
| Spermidine | 10 | 2 | 20 | 5 |
| Spermine | 10 | 2 | 20 | 5 |
| L-Alanine | 10 | 1 | 10 | 6 |
| Diaminopropane | 10 | 1 | 10 | 6 |
| L-Ornithine | 10 | 1 | 10 | 6 |

TABLE 1-continued

|  | No. of Mice Tested | No. of Mice Survived | % | Ranking |
|---|---|---|---|---|
| L-Lysine | 10 | 0 | 0 | 7 |
| L-Arginine | 10 | 0 | 0 | 7 |

EXAMPLE 2

*E. coli* LPS 0.7 mg in 1 ml PBS buffer (pH 7.4) containing one of a variety of concentrations of propylamine (0.03%, 0.1%, 0.3%) was injected intraperitoneally into mice. The survival rates were observed for three days. The results (shown in Table 2) show that there is a dose-related improvement in survival rates. The dose of 0.3% of propylamine has the best therapeutical effect. The dose above 0.3% was not as good as that of 0.1%.

TABLE 2

|  | Propylamine | | | |
|---|---|---|---|---|
| EXP NO | 0%+ | 0.03% | 0.1% | 0.3% |
| 1 | 0/3* | 1/3 | 1/3 | 2/3 |
| 2 | 2/4 | 2/4 | 4/4 | 4/4 |
| 3 | 0/3 | 2/3 | 2/3 | 3/3 |
| Total | 2/10 | 5/10 | 7/10 | 9/10 |
|  | 20% | 50% | 70% | 90% |
| P-value# |  |  | 0.1 | 0.01 |

*Survived/total mice
Analyzed by test of contingency table
+The concentration in 1 ml administered to each mouse

EXAMPLE 3

The test conditions were identical to those in Example 2 except that the compound injected was n-butylamine. The results (Table 3) show the dose of 0.1% n-butylamine has the best therapeutical effect. The dose above 0.3% was not as good as that of 0.1.

TABLE 3

|  | n-butylamine | | | |
|---|---|---|---|---|
| EXP NO | 0%+ | 0.03% | 0.1% | 0.3% |
| 1 | 1/2* | 2/2 | 2/2 | 2/2 |
| 2 | 1/4 | 3/4 | 3/4 | 3/4 |
| 3 | 0/4 | 0/4 | 4/4 | 3/4 |
| Total | 2/10 | 5/10 | 9/10 | 8/10 |
|  | 20% | 50% | 90% | 80% |
| P-value# |  |  | 0.01 | 0.05 |

*Survived/total mice
Analyzed by test of contingency table
+The concentration in 1 ml administered to each mouse

EXAMPLE 4

Different doses of L-glutamine and L-asparagine were administered to mice previously injected with LPS to protect the mice from endotoxin-induced shock. The results are shown in Table 4.

TABLE 4

|  |  | 01 mg/mouse | 1 mg/mouse | 10 mg/mouse |
|---|---|---|---|---|
| Gln | Survived/Total Mice | 6/8 | 8/8 | 7/8 |
|  | Survival Rate | 75% | 100% | 87.5% |
|  | P-value\ | <0.1 | <0.01 | <0.05 |
| Asn | Survived/Total Mice | 4/8 | 5/8 | 7/8 |
|  | Survival Rate | 50% | 67.5% | 87.5% |
|  | P-value | NS | NS | <0.05 |
| PBS | Survived/Total Mice |  | 2/8 |  |
|  | Survival Rate |  | 25% |  |

NS: No significance
\p- value was based on "PBS" dose

The effects of glutamine and asparagine on the survival rate of mice injected with LPS was measured over time, and the results are shown in Table 5 below.

TABLE 5

|  |  | −24h | −12h | 0h‡ | 1h | 3h | 6h |
|---|---|---|---|---|---|---|---|
| L-Gln | Survived/Total Mice | *6/8 | 7/8 | 7/8 | 7/8 | 1/8 | 0/8 |
|  | Survival Rate | 75% | 87.5% | 87.5% | 87.5% | 12.5% | 0% |
|  | P-value† | <0.05 | <0.05 | +0.01 | <0.05 | NS | NS |
| L-Asn | Survived/Total Mice | 5/8 | 7/8 | 8/8 | 7/8 | 1/8 | 0/8 |
|  | Survival Rate | 62.5% | 87.5% | 100% | 87.5% | 12.5% | 0% |
|  | P-value† | 0.10 | <0.05 | <0.01 | <0.5 | NS | NS |
| PBS | Survived/Total Mice | 1/8 | 2/8 | 1/8 | 2/8 | 2/8 | 1/8 |
|  | Survival Rate | 12.5% | 25% | 12.5% | 25% | 25% | 12.5% |

†P-value: to administer PBS at one tiine as comparative
‡The time LPS was administrated is designated as the zero hour; times prior to the administraiion of LPS are designated with "-"
NS: No significance The protective effect of L-glutamine, L-glutamate, L-asparagine, L-asparate on mice injected with LPS is shown in Table 6.

TABLE 6

|  | Glutamine | Glutamate | Asparagine | Aspartate | LPS* |
|---|---|---|---|---|---|
| Survived/Total Mice | 17/20 | 13/20 | 18/20 | 12/20 | 4/20 |
| Survival Rate | 85% | 65% | 90% | 60% | 20% |
| P-value | <0.061 | <0.005 | <0.001 | 0.005 |  |

L-Glutamine dose=10 mg/mouse

L-Glutamate dose=10 mg/mouse

L-Asparagine dose=10 mg/mouse

L-Aspartate dose=10 mg/mouse

LPS dose=1 mg/mouse

The invention has been described in preferred and exemplary embodiments and aspects, but is not limited thereto. Persons skilled in the art will appreciate that other modifications and applications fall within the scope of the invention. When the term "about" is used in the specification and claims in connection with a range of numbers, it is intended to modify both the low value and the high value of the range.

I claim:

1. A method for the treatment of septic shock in a patient in need thereof, comprising:

administering to the patient a therapeutically-effective amount of a composition comprising at least one compound having the formula (I):

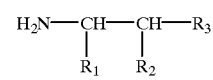

wherein:
   $R_1$ is hydrogen, hydroxyl, amino, or $C_1$–$C_8$ alkyl;
   $R_2$ is hydrogen, hydroxyl, amino, or $C_1$–$C_8$ alkyl; and
   $R_3$ is hydrogen, hydroxyl, carboxyl, amino, $C_1$–$C_8$ alkyl, phenyl, substituted phenyl, amide, or $C_1$–$C_8$ aminoalkylcarbonyl; or a therapeutically-effective salt, ester or solvate thereof.

2. The method according to claim 1, wherein $R_3$ is hydrogen, hydroxyl, carboxyl, amino, $C_1$–$C_8$ alkyl, phenyl, substituted phenyl, or amide.

3. The method according to claim 1, wherein $R_1$ is hydrogen.

4. The method according to claim 1, wherein $R_1$ is hydrogen and $R_2$ is hydrogen.

5. The method according to claim 1, wherein the composition further comprises a pharmaceutically acceptable carrier.

6. The method according to claim 5, wherein the carrier is phosphate buffered saline.

7. The method according to claim 1, wherein the composition is administered to the patient parenterally.

8. The method according to claim 1, wherein the composition is administered to the patient orally.

9. A method for the treatment of septic shock in a patient in need thereof, comprising:

administering to the patient a therapeutically-effective amount of a composition comprising at least one compound selected from the group consisting of butylamine, propylamine, diaminopropane, and diaminobutanone, and therapeutically effective salts, ester, solvates, and substitution products thereof.

10. The method according to claim 9, wherein the composition further comprises a pharmaceutically acceptable carrier.

11. The method according to claim 10, wherein the carrier is phosphate buffered saline.

12. The method according to claim 9, wherein the composition is administered to the patient parenterally.

13. The method according to claim 9, wherein the composition is administered to the patient orally.

14. The method according to claim 9, wherein the compound is n-butylamine or a therapeutically-effective salt, solvate, or substitution product thereof.

15. The method according to claim 9, wherein the compound is n-butylamine.

16. The method according to claim 15, wherein the composition is administered to the patient parenterally.

17. The method according to claim 15, wherein the composition is administered to the patient orally.

18. The method according to claim 15, wherein the composition is administered to the patient in an amount of at least about 0.05 ml/kg of body weight of the patient.

19. The method according to claim 15, wherein the composition is administered to the patient in an amount of from about 1.5 to 15 ml/kg of body weight of the patient.

20. The method according to claim 15, wherein the composition is administered to the patient in an amount of from about 5 to 15 ml/kg of body weight of the patient.

21. The method according to claim 9, wherein the compound is propylamine or a therapeutically-effective salt, solvate, or substitution product thereof.

22. The method according to claim 9, wherein the compound is propylamine.

23. The method according to claim 22, wherein the composition is administered to the patient parenterally.

24. The method according to claim 22, wherein the composition is administered to the patient orally.

25. The method according to claim 22, wherein the composition is administered in an amount of at least about 0.05 ml/kg of body weight of the patient.

26. The method according to claim 22, wherein the composition is administered in an amount of from about 1.5 to 15 ml/kg of body weight of the patient.

27. The method according to claim 22, wherein the composition is administered in an amount of from about 5 to 15 ml/kg of body weight of the patient.

28. A method for the treatment of septic shock in a patient in need thereof, comprising:

administering to the patient a therapeutically-effective amount of a composition comprising at least one compound having the formula (I):

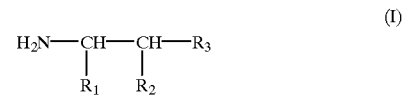

wherein:

$R_1$ is hydrogen, hydroxyl, amino, or $C_1$–$C_8$ alkyl;

$R_2$ is hydrogen, hydroxyl, amino, or $C_1$–$C_8$ alkyl; and $R_3$ is hydrogen, hydroxyl, carboxyl, amino, $C_1$–$C_8$ alkyl, phenyl, substituted phenyl, amide, $C_3$–$C_8$ aminoalkyl, or $C_1$–$C_8$ aminoalkylcarbonyl; or a therapeutically-effective salt, ester or solvate thereof.

29. A method according to claim 28, wherein $R_3$ is hydrogen, hydroxyl, carboxyl, amino, $C_1$–$C_8$ alkyl, phenyl, substituted phenyl, amide, $C_4$–$C_8$ aminoalkyl, or $C_1$–$C_8$ aminoalkylcarbonyl.

* * * * *